(12) United States Patent
Shah et al.

(10) Patent No.: US 6,280,414 B1
(45) Date of Patent: Aug. 28, 2001

(54) METHOD AND APPARATUS FOR LOCAL DELIVERY OF THERAPEUTIC AGENT

(75) Inventors: Chirag B. Shah, Nashua, NH (US); Richard A. Gambale, Tynsboro; Stephen J. Forcucci, Arlington, both of MA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/164,171

(22) Filed: Sep. 30, 1998

(51) Int. Cl.[7] .................................................. A61M 29/00
(52) U.S. Cl. ............................................. 604/104; 604/107
(58) Field of Search ..................... 604/96, 101, 104–109, 604/264, 508, 509, 523; 606/192, 194, 191, 198

(56) References Cited

U.S. PATENT DOCUMENTS

| | | |
|---|---|---|
| 5,161,534 * | 11/1992 | Berthiaume . |
| 5,554,119 | 9/1996 | Harrison et al. . |
| 5,713,860 * | 2/1998 | Kaplan et al. ........................ 604/96 |
| 5,713,863 * | 2/1998 | Vigil et al. ........................... 604/104 |
| 5,752,518 | 5/1998 | McGee et al. . |
| 5,772,590 | 6/1998 | Webster, Jr. . |

FOREIGN PATENT DOCUMENTS 0 841 040 A1    5/1998   (EP) .

OTHER PUBLICATIONS

Steven R. Bailey, *Mechanisms of Delivery and Local Drug Delivery Technologies*, Semin Intervent Cardiol 1996, pp. 17–23.

* cited by examiner

Primary Examiner—Sharon Kennedy
(74) Attorney, Agent, or Firm—Sterne, Kessler, Goldstein & Fox P.L.L.C.

(57) ABSTRACT

The present invention provides a device and method for delivering a therapeutic substance to a treatment site within a patient such as a vessel that has undergone angioplasty. The device provides flexible conduits placed together in the vessel along with a shaft that is attached to their distal ends. After being navigated to the treatment site, the shaft may be moved relative to the conduits causing them to buckle and bow radially outward into contact with the tissue to be treated. The therapeutic substance is then pressurized to be delivered through perfusion ports along the distal portion of the conduits. Because the conduits can be expanded into contact with the treatment site without the assistance of an inflatable member, blood flow through the region during delivery of the therapeutic substance is not interrupted in any significant way. Alternatively, the present invention may be used in conjunction with a balloon angioplasty catheter to deliver therapeutic substances after the dilatation procedure. As with the first embodiment, the delivery conduits may be expanded independently from the dilatation balloon so that blood flow will not be interrupted during delivery of the therapeutic substance.

33 Claims, 6 Drawing Sheets

METHOD AND APPARATUS FOR LOCAL DELIVERY OF THERAPEUTIC AGENT

FIELD OF THE INVENTION

This invention relates to a device and method for delivering a therapeutic substance to a treatment site within a patient. More particularly, the device and method are useful for delivering therapeutic drugs to the site of a vessel which has undergone an angioplasty procedure.

BACKGROUND OF THE INVENTION

In treatment of specific areas or organs of the human body with drugs or other therapeutic substances, it is preferable to provide the therapeutic substance only to the area that needs treatment, rather than delivering the substance generally through the blood stream. Localized delivery of a therapeutic substance avoids any undesirable effects that the substance may have on other areas of the body that do not need treatment. Furthermore, localized delivery provide the intended treatment site with a more concentrated dose of the therapeutic substance because it has not been diluted during its travel through the blood stream. Thus, the treatment can be more effective. An additional benefit of localized delivery is that a reduced quantity of the substance can be used to treat the intended location than would otherwise be required to supply a patient's entire blood stream with a quantity sufficient to create a beneficial concentration of the substance for the intended treatment site. The reduction in required quantity results in substantial savings in cost associated with the treatment, especially where the therapeutic substance is an expensive pharmaceutical.

In treatment of vessels for coronary artery disease, stenosed regions are frequently treated by direct delivery of a therapeutic substance. Commonly, the stenosed area of the vessel is first dilated with an angioplasty balloon catheter prior to or during the delivery of the therapeutic substance. The objective of localized drug treatment of the vessel after angioplasty is to reduce the rate of restenosis, or reclosure of the vessel. Vessels which have undergone angioplasty frequently suffer from restenosis, an abrupt closure of the vessel which quickly blocks the flow of blood and can be fatal. Therefore, drugs such as anti-coagulants are applied to an area of the vessel which has recently undergone angioplasty, usually immediately following the procedure.

A common mechanism for delivering a therapeutic substance to an internal location such as a vessel that has recently undergone angioplasty has been delivery through a porous balloon catheter. Generally, such catheters are configured similar to conventional dilatation balloon catheters with the modification of small holes formed into the balloon through which may flow a therapeutic substance under pressure. The substance is also used as the inflation medium for the balloon. Although the inflated balloon places the perfusion outlets in close proximity to the vessel wall to be treated, expulsion of the therapeutic substance necessarily requires inflation of the balloon, which temporarily blocks the blood vessel being treated. Interruption of blood flow through the vessel is undesirable because it can cause pain and discomfort to the patient. Also, delivery through a porous balloon limits the choice of agents that may be delivered as it is undesirable to mix multiple therapeutic agents within the single inflation lumen and balloon of the delivery catheter.

Variations of the porous balloon concept have been provided in an attempt to address the shortcomings of the porous balloon. Balloons have been disclosed that have multiple lumens extending through or on the balloon wall which contain and perfuse therapeutic substances independent of the inflation medium used to expand the body of the balloon. Some of these devices provides means for delivering more than one substance simultaneously. U.S. Pat. No. 5,713,860 (Kaplan et al.) discloses an infusion catheter having an inflatable member over which may be applied several lumens containing one or more therapeutic substances. Because it is important to present the source of therapeutic substance as close as possible to the intended treatment site, the conduits disclosed in the Kaplan patent are expanded by an inflatable member to be in close proximity to the vessel wall. The inflatable member is provided with slits which form into passageways to permit some blood flow through the area when the member is expanded during drug delivery. However, the inflatable member occupies a sizable cross-sectional area of the vessel when expanded, which may serve to interrupt blood flow during drug delivery.

It would be desirable to provide a device for localized delivery of a therapeutic substance, particularly for use in a vessel, which is configured to permit expansion of delivery conduits into close proximity of or in contact with the treatment site without inflation of a balloon which may serve to restrict blood flow through the treatment area. It is an objective of the present invention to provide such a device.

SUMMARY OF THE INVENTION

The present invention provides a therapeutic substance delivery device and method which provides for the positioning of at least one delivery conduit in close proximity with the intended treatment site independent of the expansion of an inflatable member such as a balloon. The embodiments of the present invention utilize at least one flexible conduit which can be buckled to form a bowed configuration to place its perfusion ports in close proximity to tissue such as a vessel to be treated. The delivery device may be used with or without a balloon angioplasty catheter to provide immediate delivery of a therapeutic substance after an angioplasty procedure. It is noted that throughout the discussion of the present invention that proximal refers to the direction along the delivery path of the device leading to the exterior of the patient and distal refers to the path along the delivery device leading to the interior of the patient.

In one embodiment of the present invention, one or more flexible tubes or conduits are arranged to extend parallel with a shaft such as a wire or flexible hypotube. The distal ends of the conduits are joined to the distal end of the shaft in an end cap while the more proximal regions of the shaft and conduits are held in parallel relationship to one another within a multi-lumen outer catheter, each of the conduits and shaft slidably contained within a separate lumen of the catheter. The proximal ends of the conduits may be joined to one or more sources of therapeutic substances which are intended to be delivered to the treatment site. Distal portions of the conduits not contained in the outer catheter have perfusion ports along their length and can bow radially outward under longitudinally compressive loading applied by moving the shaft relative to the conduits.

The assembly may be navigated through the vessels to the treatment site much as would be a conventional catheter. During delivery, the conduits may be held in tension to extend substantially parallel to the longitudinal axis of the shaft along their entire length. However, the distal portions of the conduits are expandable to be in close proximity to the treatment site by sliding the shaft and conduits relative to each other. Specifically, relative movement of the shaft in a proximal direction relative to the conduits, or movement of the conduits in a distal direction relative to the shaft, causes the shaft to be placed in tension while the conduits are placed in compression. Thus, the flexible conduits buckle in a region where they are not supported by the outer catheter. By placing the distal end of the outer catheter proximal to the distal end of the shaft and conduits, an expandable array of distal portions of the conduits is created. Perfusion ports formed along the distal portion of the conduits along their radially outward facing side permits the ejection of a therapeutic substance into or in close proximity to the wall. Delivery of the substance close to the wall of the vessel prevents the substance from being washed away with the flow of blood because the velocity profile of blood flowing through a vessel is such that flow near the vessel wall is minimal. In addition, the conduits may be expanded at a location slightly upstream of the treatment site so that the flow of blood will carry the substance to the intended location.

The delivery device described above may be modified by joining the conduits to the catheter in which they are contained so that they may be manipulated as a group to be slid relative to the shaft to cause buckling and expansion of their distal portions. Once expanded, a lock device may be applied to the shaft where it protrudes from the proximal end of the outer catheter to prevent further relative movement of the conduit. The lock may comprise a conventional guidewire steering handle clamped on the shaft to prevent movement of the shaft into the outer catheter and relative to the conduits. Another suitable lock may comprise a sleeve which engages the proximal end of the outer catheter at one end and engages a hub or ring attached to the proximal end of the shaft at its other end to maintain a spaced relationship between the outer catheter and the conduits and prevent relative movement of the conduits relative to the shaft. Alternatively, the shaft may be joined to the outer catheter while the conduits remain slidable relative to the catheter.

The conduits need not extend the entire length of the shaft, but rather may extend from a manifold placed at some point along the length of the outer catheter and supplied by a single supply tube which extends to the proximal end of the device to be joined to a supply of a therapeutic substance outside of the patient. Alternatively, additional supply tubes could feed a manifold having a plurality of conduits extending therefrom to provide the ability to supply different therapeutic substances simultaneously.

Another embodiment of the delivery device uses a shaft having a lumen, such as provided by use of hypodermic tubing for the shaft, to permit the therapeutic substance to be delivered through the shaft to a distal manifold joined to the distal ends of the conduits. Therefore, rather than supplying a therapeutic substance to the proximal ends of the conduits, the substance is first delivered to the distal end of the shaft and pressurizes the conduits from their distal ends in a flow traveling in the proximal direction. In this embodiment, the proximal ends of the conduits are sealed and joined to an outer catheter shaft that is slidable relative to the hypotube shaft. In another embodiment, a shaft of a balloon catheter may be used as the shaft to provide the ability to dilate a vessel and immediately apply a therapeutic substance to the treatment site. In one embodiment of the dilatation catheter and delivery device combination, the distal ends of the conduits are joined to the exterior of the dilatation catheter shaft at a location proximal to the balloon. The more proximal regions of the dilatation catheter and conduits may be contained within an outer catheter having multiple lumens to contain each of the conduits and balloon catheter. After dilating the vessel in a conventional manner, the assembly may be moved distally so that the expandable distal portions of the conduits are in position at the treatment site to deliver the therapeutic substance directly to the stenosis. Alternatively the assembly may remain in its original position and therapeutic substance may be delivered proximal (upstream) of the treatment site and permitted to be carried by blood flow to the treatment site. Prior to perfusion of the therapeutic substance, the distal portions of the conduits may be expanded radially outward from the catheter shaft by relative movement of the balloon catheter shaft and conduits similar to the operation of the first embodiment described above.

In another embodiment of the present invention employing a dilatation catheter, the conduits are joined at their distal ends to a ring which is slidable over the shaft of the dilatation catheter. The dilatation catheter has a stop formed at the distal end of its shaft, distal to the balloon, which is formed to catch the slidable ring to arrest its distal motion over the catheter shaft and cause the distal portions of the conduits to buckle and expand radially outward as distal forces continue at their proximal ends. Thus, in use after dilatation with the balloon catheter, the entire assembly need not be moved distally, past the site of the stenosis within the vessel. Rather, the expandable conduits are slid distally on the catheter shaft, over the location of the deflated balloon, and expanded by relative movement of the shaft and conduits to deliver a therapeutic substance to the treatment site. Avoiding movement of the deflated dilatation balloon distal to the stenosis eliminates the risk of the catheter balloon becoming caught by the narrowed vessel which could make its withdrawal from the patient difficult.

In each embodiment, the conduits may be formed to assume a spiral configuration as they bow outward under longitudinal compressive force. The spiral configuration occurs over a short length and, therefore, may not encompass a full 360° rotation around the axis about which it is formed. However, the spiral shape of each conduit extends the circumferential reach around the inside of the vessel to which a therapeutic substance is delivered. Additionally, with each of the above-embodiments, the conduit and shaft assembly of the delivery device may be rotated within the vessel during delivery of the therapeutic substance to ensure that the conduits inject a stream of the substance near all radial portions of the vessel intended to be treated. A further modification of the above devices includes radial extending projection tubes provided at each perfusion port to penetrate the vessel wall as the conduits expand radially outwardly from the shaft during delivery of the substance. The therapeutic substance travels through the ports and through the projecting tubes and is injected directly into the vessel wall.

It is an object of the present invention to provide a therapeutic substance delivery device having at least one delivery conduit which may be expanded to be in close proximity to a tissue treatment site without assistance from an inflatable member to provide minimal obstruction to blood flow through the vessel during the substance delivery.

It is another object of the invention to provide a therapeutic substance delivery device that can be used in combination with a dilatation catheter to deliver a therapeutic substance immediately following a balloon dilatation procedure to the treatment site.

It is another object of the invention to provide a therapeutic substance delivery device that can provide simultaneous delivery of more than one substance to a treatment site.

It is yet another object of the invention to provide a method of delivering a therapeutic substance to a treatment site which does not require the expansion of an inflatable member to move the substance delivery conduits into proximity with the treatment site.

BRIEF DESCRIPTION OF THE DRAWINGS

The foregoing and other objects and advantages of the invention will be appreciated more fully from the following further description thereof, with reference to the accompanying diagrammatic drawings wherein.

DESCRIPTION OF THE ILLUSTRATIVE EMBODIMENT

Figure 1:
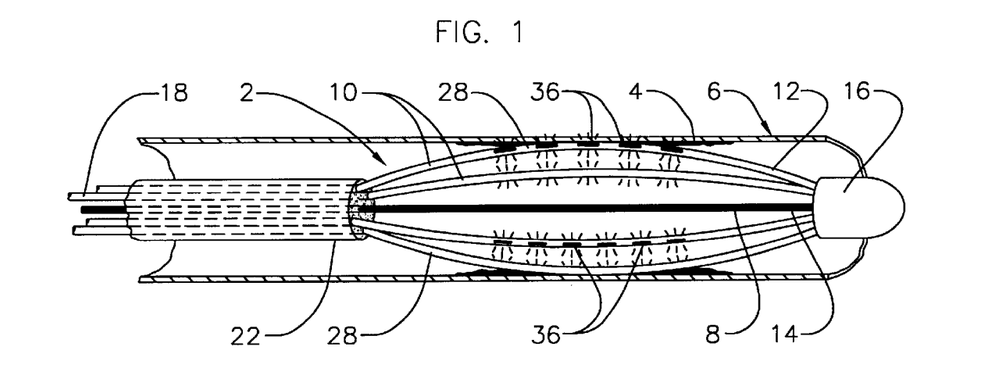
FIG. 1 is a cut-away view of a vessel into which the therapeutic substance delivery device of the present invention has been inserted.
Figure 2:
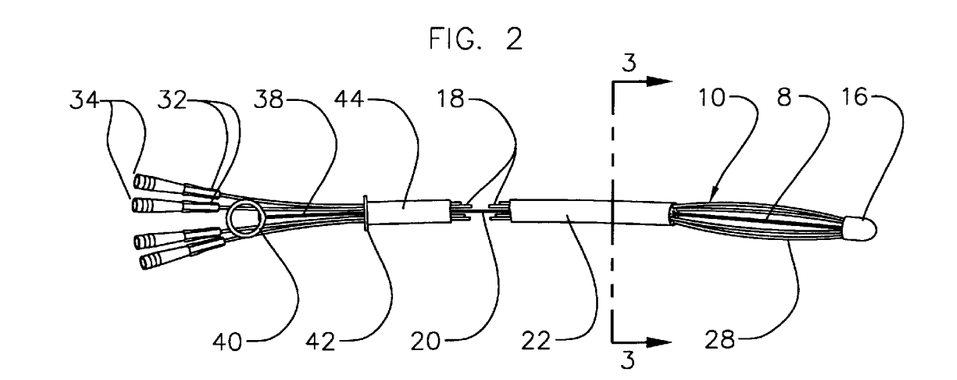
FIG. 2 is a side view of an embodiment of the therapeutic substance delivery device.

FIG. 1 shows the therapeutic substance delivery device 2 positioned within a vessel 6 adjacent a treatment site 4. The device is comprised of an elongate shaft 8 surrounded by at least one, but preferably a plurality of flexible conduits 10. As shown in FIG. 2, the conduits extend along an axis that is substantially parallel to the axis of the shaft over their length. The conduit are formed from flexible tubing such as polyethylene, PET or pelethane and have an outside diameter on the order of 0.010". The length of the shaft is on the order of the length for conventional angioplasty catheters: on the order of 110–150 cm. The shaft may be made from stainless steel hypotubing or an extruded polymer and may have an outside diameter on the order of 0.045". The distal end 12 of each conduit 10 is joined to the distal end 14 of the shaft. The joint between the distal end of the conduits 12 and the distal end of the shaft 14 may be an adhesive joined and formed into an end cap 16 having a rounded surface to provide an atraumatic profile as the device is navigated through the vessels. The proximal portion 18 of the conduits and proximal portion of the shaft 20 may be contained in an outer catheter 22 to help maintain the conduits and shafts in parallel relationship.

Figure 3:
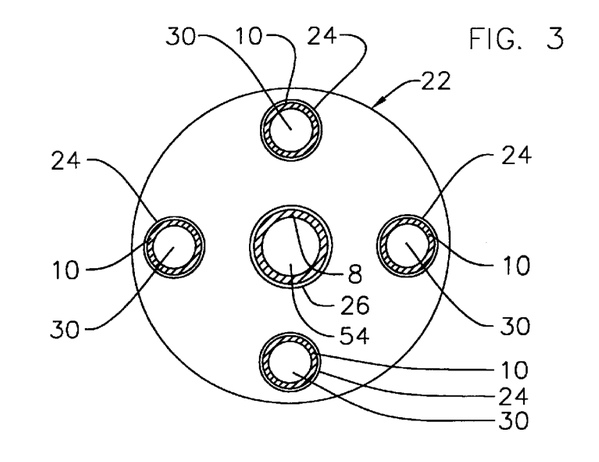
FIG. 3 is a cross-sectional view of the therapeutic substance delivery device as viewed along the line 3—3 of FIG. 2.

The outer catheter shaft 22 is of conventional polymer construction and may have several lumens as shown in the cross-sectional view of the catheter, shaft and conduit assembly shown in FIG. 3. The catheter has four outer lumens 24 sized to receive the conduits and a central lumen 26 sized to receive the shaft, however, a variety of catheter configurations could be used to retain the conduits 10 and shaft 8 in parallel relationship to each other. The shaft may have an outer diameter on the order of 0.080"–0.090"

In the current example, each outer lumen 24 contains a flexible conduit and the central lumen 26 contains a shaft 8. Either the conduits or the shaft may be fixed within the catheter 22; however, the proximal portion of the shaft 20 and conduits 18 should be longitudinally slidable relative to each other to permit the bowing of the conduit distal portions 28 as will be described below in further detail.

Figure 12:
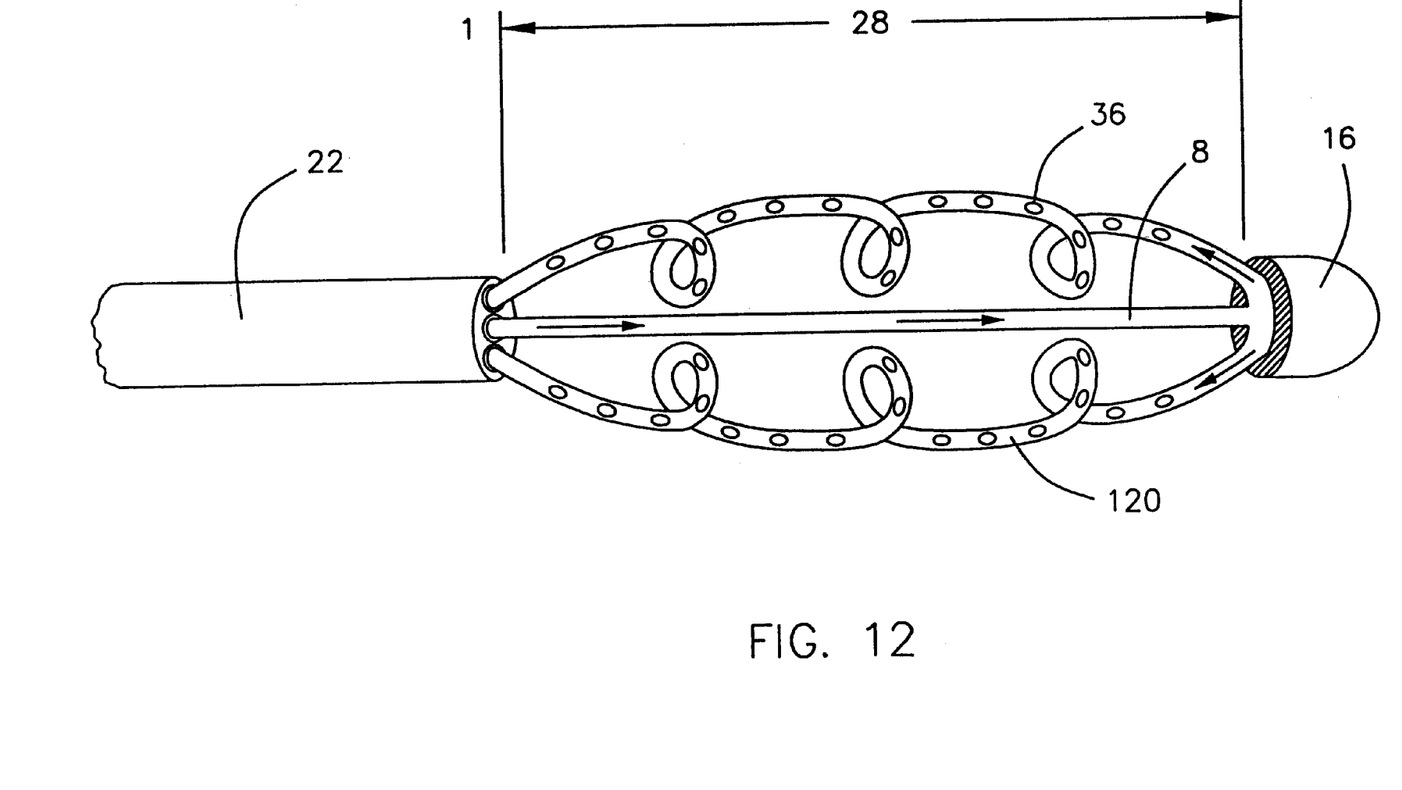
FIG. 12 is a perspective view of an alternate embodiment of the therapeutic substance delivery device of the present invention.

The distal portion 28 of the conduits should remain uncovered by the outer catheter 22 so that the flexible conduits will buckle and bow in a radially outward direction from the central axis defined by the shaft 8 when the shaft is moved relative to the conduits. An uncovered length of between 10–60 mm is adequate to permit bowing of the conduits. Specifically, because the distal ends 12 of the conduits are joined to the distal end 14 of the shaft, the unsupported distal portion 28 of the conduits will buckle and tend to bow in a radially outward direction from the shaft 8 when they are placed in longitudinal compression. A compressive load can easily be placed on the conduits by pulling the shaft 8 in a proximal direction and/or pushing the conduits in a distal direction such that there is relative movement between the conduits and the shaft. Thus, the delivery conduits of the present invention may be expanded radially outward to be adjacent to a treatment site such as the interior of a vessel 6 without the assistance of an inflatable member, such as a balloon providing the radially expansive force to the conduits. The length of the distal portion of the conduits, which bow outward may be on the order of 10–60 mm to provide sufficient perfusion area. Additionally, as shown in FIG. 12 the conduits may be heat set during their manufacture to have a spiral configuration 120 when they are bowed outwardly during delivery of the therapeutic substance. The spiral configuration of each conduit may provide improved coverage, radially around the vessel.

Each conduit 10 has a lumen 26 through which passes a therapeutic substance to be delivered to the treatment site. The lumen may be on the order of 0.005" in diameter. A variety of therapeutic substances may be delivered with the present invention. By way of example, when delivering substances to prevent restenosis following an angioplasty procedure, anti-coagulants, such as heparin may be delivered to a treatment site. Liquid therapeutic substances can be introduced at the proximal end of the conduits 32. Luer fittings 34 at the proximal ends of the conduits may be joined to individual sources of therapeutic substances so that different substances can be delivered to the treatment site simultaneously. Perfusion ports 36 are formed in the distal portion 28 of the conduits, which flex outward to be adjacent the treatment site 4. The perfusion ports may be on the order of 0.005 inch and may be formed by a punch drill or laser into the conduit tubes. A plurality of such perfusion ports are placed on the radially outward facing surface of each conduit so that when the conduit is expanded radially, the therapeutic substance ejected through the perfusion ports will either be very close to or directly applied to the treatment site 4 such as the interior of a vessel 6 as shown in FIG. 1. It is anticipated that most therapeutic substances delivered through the delivery device will have a relatively light viscosity making the fusion ports adequate for appropriate flow of the substance. However, it should be recognized that the size of the perfusion ports can be modified to regulate flow of substances having a range of viscosities.

To facilitate application of a compressive force on the conduits 10, the conduits may be bonded by adhesive to the outer catheter 22 to prevent relative movement between them. However, in this configuration, the shaft 8 must remain slidable through the central lumen 26 of the catheter so that it remains movable with respect to the conduits 10. In this configuration, the proximal end of the shaft 38 may have a pull ring 40 or some other device to facilitate grasping so that the shaft may be pulled in a proximal direction and/or conduits moved in a distal direction relative to the shaft to cause expansion. Additionally, a proximal stop 42 may be formed at the proximal end 44 of the outer catheter 22 to further facilitate grasping and creating relative movement between the shaft and conduits.

Figure 4:
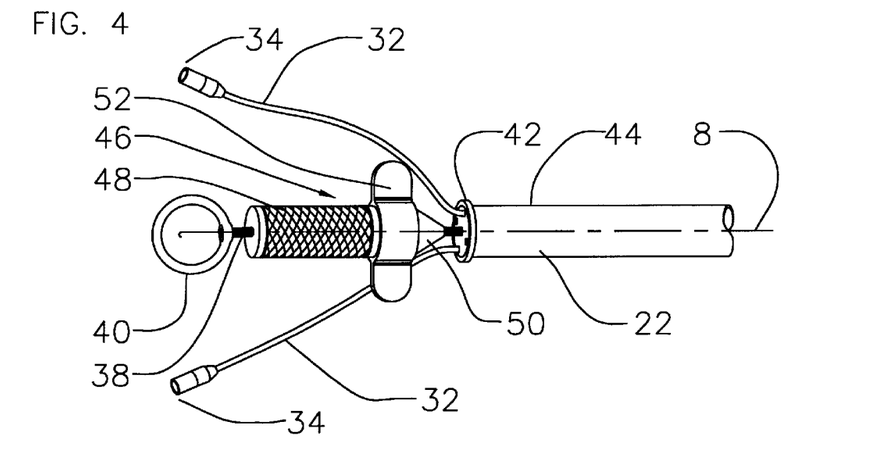
FIG. 4 is a side view of a portion of the therapeutic substance delivery device having a lock applied.

To maintain the conduits in their expanded configuration the lock 46 may be joined to the proximal end 38 of the shaft 8 as shown in FIG. 4. The lock may comprise a conventional guidewire steering handle 48 comprising a nut 52 and collet 50 which can be tightened to clamp on the shaft 8. So mounted, the collet 50 of the steering handle 48 will abut the proximal stop 42 of the outer catheter 22 to resist sliding movement of the shaft 8 relative to the catheter 22 and conduits that are bonded to it. Thus, the conduits 10 will remain in compression, which causes the distal portions 28 of the conduits, which are unsupported by the outer catheter 22, to remain in a bowed configuration. Alternatively, a rigid sleeve (not shown) of high density plastic may be slipped over the proximal end 38 of the shaft 8 to maintain the relative position of the shaft and conduits. The length of the sleeve is equivalent to the amount of relative movement required between the shaft 8 and conduits 10 to sustain a bowed condition through a portion of the conduit.

Figure 5:
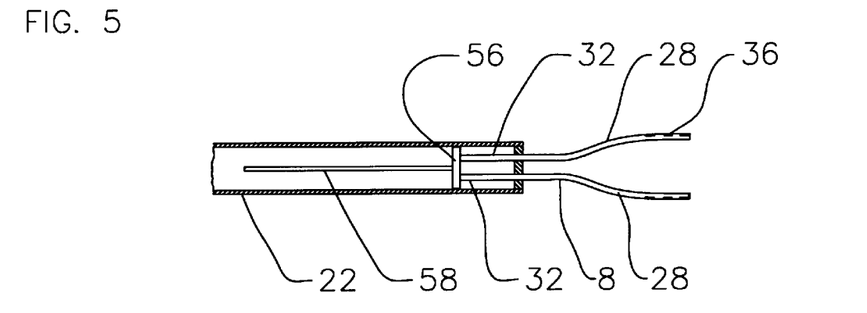
FIG. 5 is a cut-away view of a portion of the therapeutic substance delivery device showing an arrangement for a manifold.

FIG. 5 shows an alternate embodiment of the therapeutic substance delivery device. In FIG. 5, the full length conduits 10 are significantly shortened and joined to a manifold 56 which is in fluid communication with a single delivery tube 58, which extends proximally to be joined to a source of a therapeutic substance. The single delivery tube 58 fills the manifold 56 with therapeutic fluid under pressure which then is forced into the proximal ends 32 of delivery conduits 10 and then out through perfusion ports 36 as with the previously discussed embodiment. Use of a manifold 56 placed close to the distal portion of the conduits 10 not only reduces complexity of the outer shaft 22 by eliminating the number of conduits passing through it, but also reduces the quantity of therapeutic substance required to pressurize the distal portions 28 of the conduits. Less therapeutic substance is required because only a single delivery tube need be filled to pressurize the conduits as opposed to filling and pressurizing a full length tube for each conduit as would be required for the four conduit embodiment described above in connection with FIG. 1.

A limitation concerning the use of a manifold is the ability to supply different therapeutic substances simultaneously through the proximal portions of the conduits 10 because only one supply tube is receiving the therapeutic substance to be distributed to the conduits through the manifold 56. However, the manifold can be configured to have interior passages capable of separating more than one therapeutic substance and relegating that substance to a given supply tube and outlet to a given conduit or pair of conduits. In this configuration more than one supply tube could be joined to the manifold 56 so that multiple therapeutic substances could be delivered simultaneously. For example, if four delivery conduits 10 are used at the distal end of the device, and two delivery tubes 58 are used to bring in two different therapeutic substances to the manifold 56, the manifold could be configured so that each therapeutic substance would be delivered through two conduits.

In such embodiments where the conduits need not extend through round lumens 24 of an outer catheter shaft 22 due to the presence of a manifold 56, the conduits 10 may be configured to have a wider cross-sectional profile. For example, the conduits may be strips having a rectangular or oval shape profile to provide a broader surface for contacting the treatment site 6 during delivery of a therapeutic substance. In the case of the conduit configured as a strip, the perfusion ports 36 may be spaced laterally as well as longitudinally along the length of the widened conduit surface to provide a broader area of coverage at the treatment site. The strips may have a variety of cross sectional shapes. By way of example, a strip having a rectangular cross section may measure 0.003" by 0.005".

Figure 6:
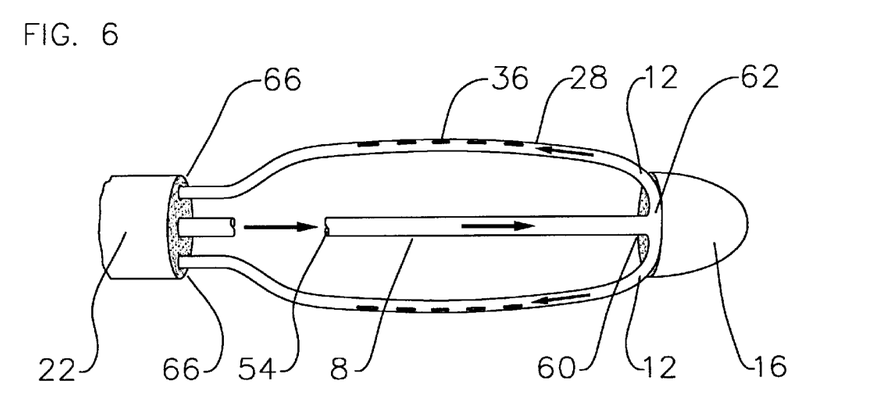
FIG. 6 is a side view of an alternate embodiment of the therapeutic substance delivery device.

As shown in FIG. 6, the shaft 8 is configured to define an interior lumen 54 extending through its length and configured to carry a therapeutic substance. The shaft of this embodiment may be a flexible stainless steel hypotube having an inside diameter on the order of 0.022 inch. In this configuration, a separate delivery tube is not needed to carry the therapeutic substance from the proximal end of the device to the distal portion 28 of the conduits 10. Rather, the distal end 60 of the hypotube shaft may terminate at a junction 62 that is in fluid communication with the distal ends 12 of the conduits 10. A pressurized source of the therapeutic substance is joined to the proximal end of the hypotube shaft 8 for delivery to the distal end 60 of the shaft where the therapeutic substance travels into the distal portions 28 of the conduits. To pressurize the distal portions 28 of the conduits, they may be sealed at their juncture with 66 the outer catheter 22. The hypotube may be slidably moved within the outer catheter 22, as was the shaft in the above-described embodiments, to cause the conduits to be placed in compression so that they bow radially outward to approach the treatment site of a vessel wall.

Figure 7:
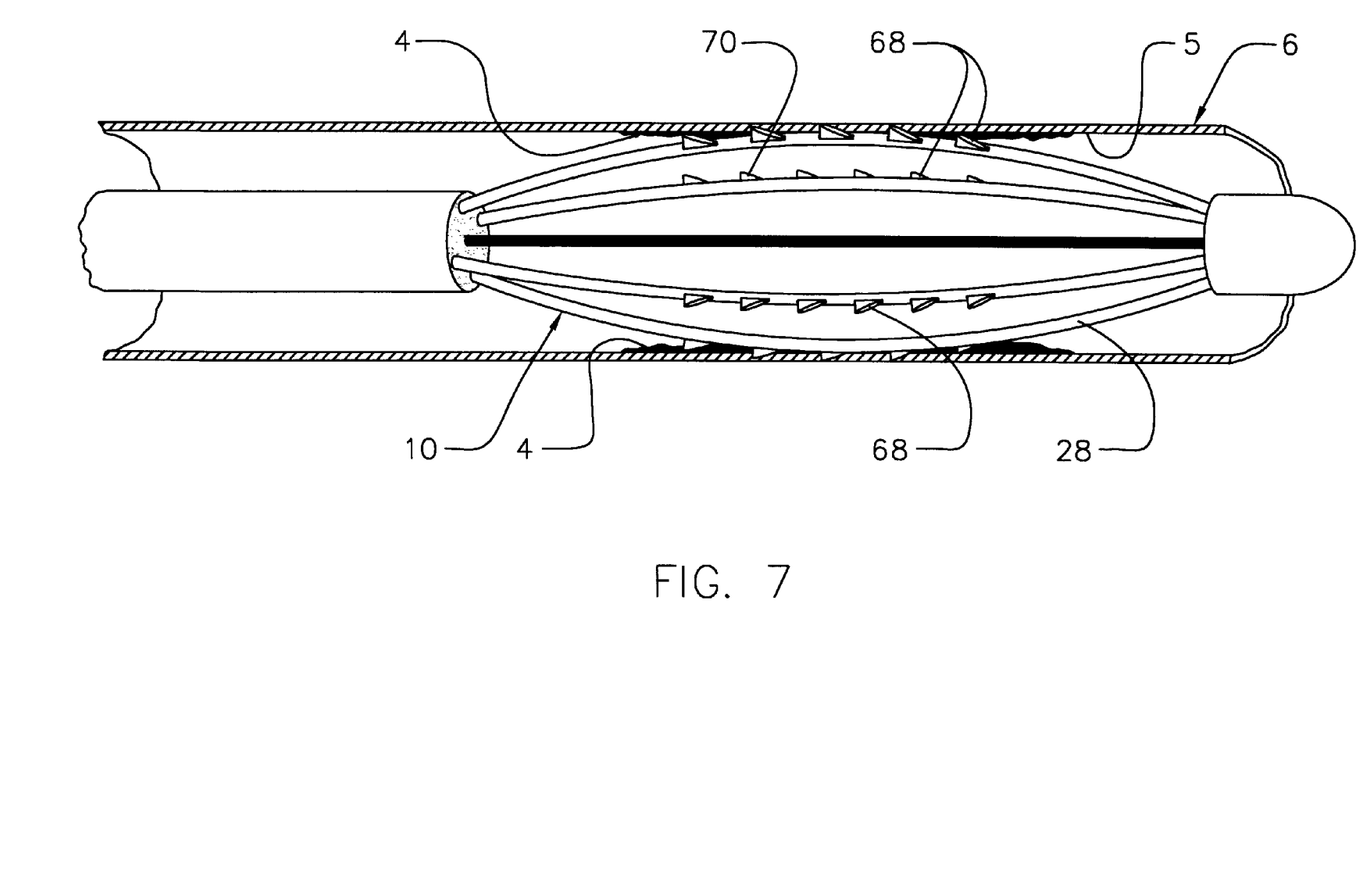
FIG. 7 is a cut-away view of a vessel into which has been inserted a modified embodiment of the therapeutic substance delivery device having piercing tubes.
Figure 8:
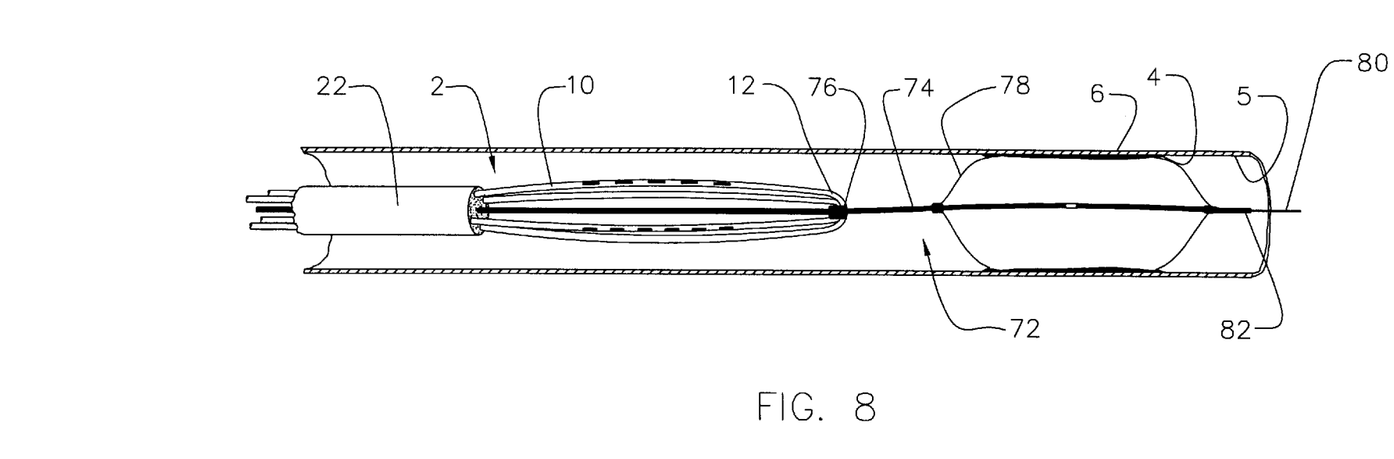
FIG. 8 is a cut-away view of a vessel into which has been inserted the therapeutic substance delivery device and an angioplasty balloon catheter in combination wherein the balloon is inflated to dilate a stenosis in the vessel.

FIG. 7 shows another variation of the therapeutic substance delivery device having piercing tubes 68 extending radially outward from the perfusion ports 36 along the distal portion 28 of conduits 10. The piercing tubes may be formed from a high density polymer, being fairly rigid and capable of maintaining a sharp point 70 to pierce the tissue of the conduits 28 are expanded in their bowed configuration and brought into contact with the inside vessel wall 5. The piercing tubes may be bonded to the perfusion ports by epoxy or other adhesives suitable for polymer materials. Once the conduits are expanded to their bowed configuration, the sharp tip 70 of the piercing tubes penetrates the inside vessel wall 5 so that the therapeutic substance is delivered directly into the vessel without risk of its being carried away by blood flow through the vessel. The piercing tubes may be configured in a variety of ways to present a sharp tip 70. The slash cut piercing tubes shown in FIG. 7 are merely exemplary, however, the tubes may be configured to have a sharpened tip at their center, similar to an arrowhead or any other sharp tip configuration. Additionally, the piercing tubes may vary in length to match the differences in length required to reach the vessel wall due to the bowed shape of the conduit upon which they are aligned. For example, the center piercing tube on a given conduit 10 may have the shortest length of the piercing tubes on that conduit while the end piercing tubes have the longest length because they are oriented on a portion of the conduit that is bowed away from the surface of the vessel wall 5. Although the addition of piercing tubes to the perfusion ports of the conduits may help insure that the therapeutic substances delivered to its intended location, it is believed that therapeutic substances can be adequately delivered to the surface of a vessel wall 5 or expelled near the vessel wall to achieve an adequate therapeutic benefit. Substances released very close to the vessel wall are believed to be absorbed by the wall without being carried away because the velocity profile of blood flowing through the vessel indicates that velocity of fluid near the wall is minimal.

The therapeutic substance delivery device of the present invention may also be used in conjunction with a balloon angioplasty catheter 72 as is shown in FIGS. 8–11. In a first arrangement, shown in FIGS. 8 and 9, the distal ends of the conduits 12 are joined and sealed directly to the balloon catheter shaft 74 at a permanent joint 76 in the same manner that the distal ends of the conduits are joined to the shaft 8 in the previous embodiments described above. The joint may be formed with adhesive suitable for polymers such as epoxy. The balloon catheter otherwise may be made of conventional construction well known in the art. The balloon catheter shaft 74 may be of conventional multi-lumen construction having an outside diameter of approximately 0.022 inch and having an inflatable balloon 78 mounted adjacent its distal end 82. The balloon catheter may have a deflated profile on the order of 0.040 inch and may have a guidewire lumen having an inside diameter on the order of 0.018 inch. A guidewire 80 may be inserted through the guidewire lumen of the balloon catheter to help navigate the assembly through the vessels to the treatment site 4 within the vessel 6. In operation of the therapeutic substance delivery device 2, the catheter shaft 74 performs the same functions that shaft 8 performs in the first embodiment.

Figure 9:
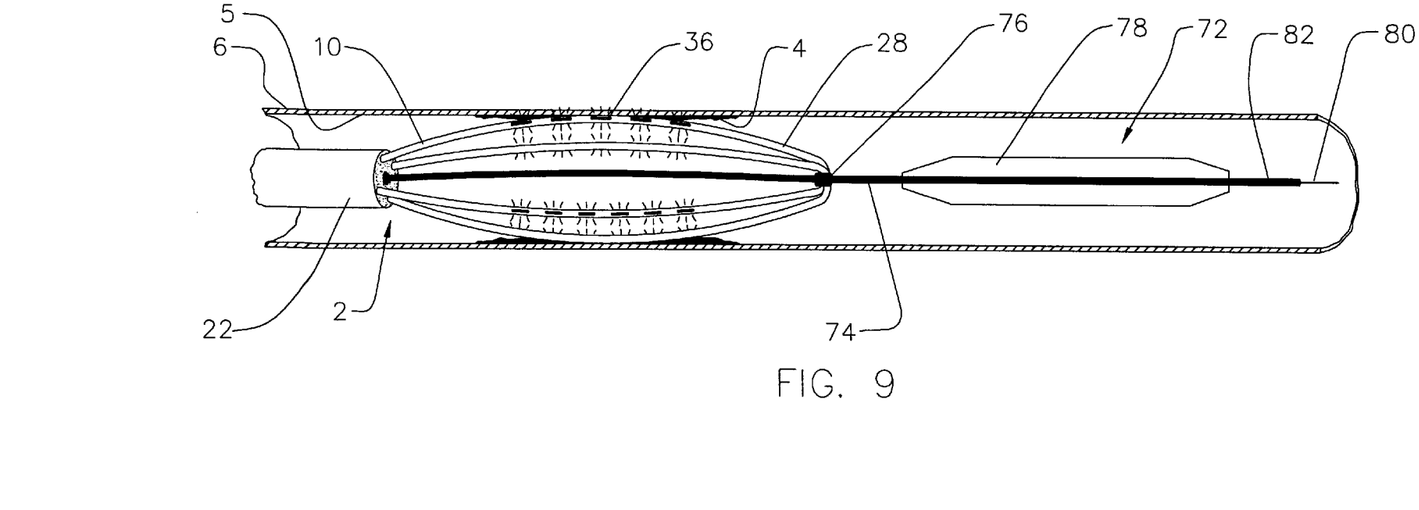
FIG. 9 is a cut-away view of a vessel into which has been placed the therapeutic substance delivery device and an angioplasty balloon catheter in combination wherein the balloon is deflated and the delivery device is delivering a therapeutic agent to the site of the stenosis.

In use, the balloon catheter and delivery device are navigated to the treatment site 4 within a vessel 6 through a guide catheter (not shown) with both the balloon 78 and conduits 10 in their low profile unexpanded configuration. Upon reaching the treatment site 4, the balloon 78 is positioned within the site (such as a stenosis) and inflated with an inflation medium carried through a lumen in the balloon catheter shaft 74 which is independent and independently inflated from the delivery conduits 10. The balloon catheter operates wholly independently from the delivery device aside from the connection 76 between the distal ends 12 of the conduits and the balloon catheter shaft 74. After the stenosis has been expanded at the treatment site 4 by the inflated balloon 78, the balloon is deflated and the delivery system and balloon catheter assembly advanced distally as is shown in FIG. 9, so that the distal portion 28 of the conduits is then aligned in the treatment site 4. While maintaining the conduits in alignment with the treatment site, a compressive force is applied to the distal portions 28 of the conduits by withdrawing the catheter shaft 74 in a proximal direction and/or advancing the outer catheter 22 and proximal portions 18 of the conduits 10 in a proximal direction. The resulting compressive force causes the distal portions 28 of the conduits 10 to bow radially outward from the catheter shaft 74 to be in contact with or in close proximity to the inside surface of the vessel wall 5 as is shown in FIG. 9. In the expanded configuration, one or more therapeutic substances may be delivered to the treatment site 4 while blood moving through the vessel 6 may pass freely through the relatively small profile of the conduits 10 and pass the deflated balloon 78. Alternatively, the catheter and delivery device combination may be left in position after dilatation and the conduits expanded and substance delivered to the vessel proximal (upstream) of the treatment site 4. Blood flow, though minimal near the vessel wall will carry the substance to the treatment site.

Figure 10:
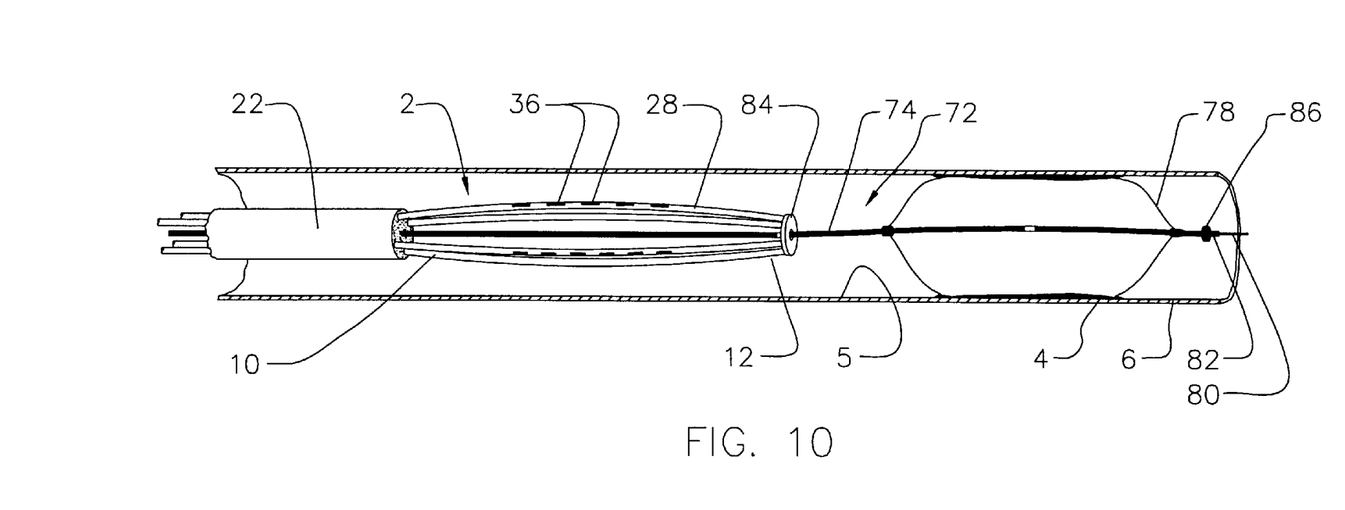
FIG. 10 is a cut-away view of a vessel into which has been inserted an alternate arrangement of the therapeutic substance delivery device and an angioplasty balloon catheter wherein the balloon is inflated to dilate the stenosis within the vessel.
Figure 11:
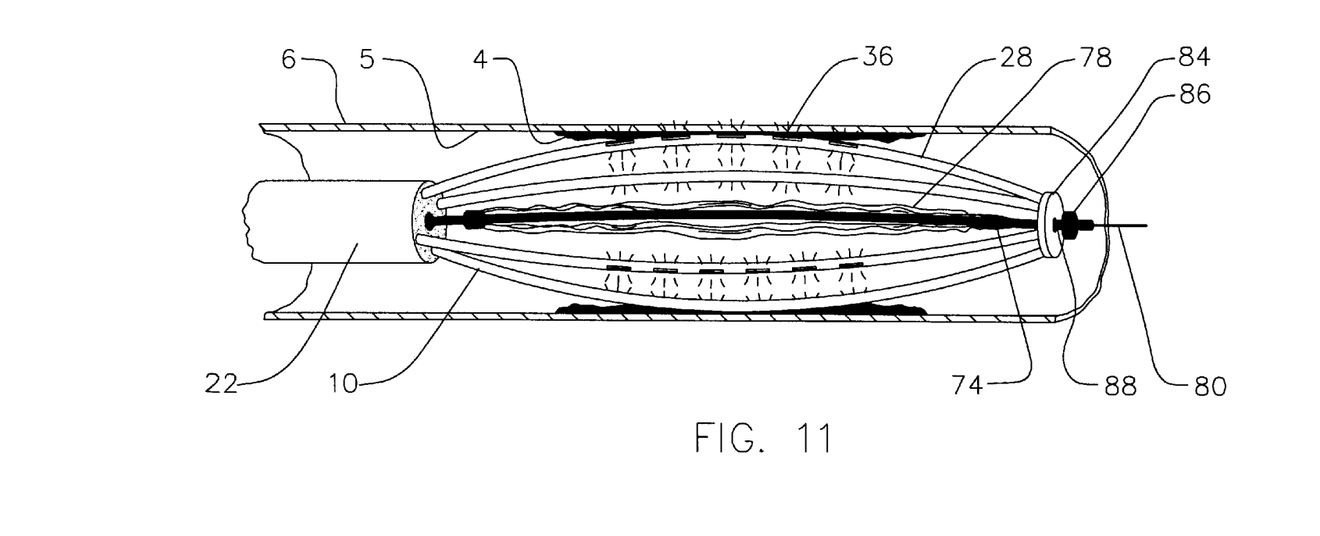
FIG. 11 is a cut-away view of a vessel into which has been inserted an alternative arrangement of the therapeutic substance delivery device in combination with an angioplasty balloon catheter wherein the balloon is deflated and the delivery device has been placed over the deflated balloon and is delivering a therapeutic substance to the location of the stenosis.

In an alternate configuration, shown in FIGS. 10 and 11, the conduits of the delivery device may be moved distally over the deflated balloon after an angioplasty procedure to deliver a therapeutic substance to the treatment site 4. Such an arrangement may be preferable where there is a serious risk that a deflated balloon moved distal to the stenosed treatment site 4 may become lodged and difficult to draw a back proximally through the stenosed area. Rather than joining the distal ends 12 of the conduits 10 directly to the catheter shaft 74, the distal ends 12 are sealed and bonded to a ring 84 that is slidable over the balloon catheter shaft 74. The ring 84 has an inside diameter 88 that is large enough to permit sliding over the balloon catheter shaft 74, as well as the balloon 78 while in its deflated profile as represented in FIG. 11. However, the ring, i.e., its inside diameter 88, is selected to be smaller than the outside diameter of distal stop 86, which is formed adjacent the distal end 82 of the balloon catheter shaft 74. The distal stop 86 may be formed from a globule of adhesive such as epoxy applied to the outside of the balloon catheter shaft. The ring 84 may be formed from a rigid material such as a high density polymer. Therefore, the outer catheter 22 and conduits 10, including their distal ends 12, are permitted to slide relative to the catheter shaft, but the distal movement of the distal ends 12 of the conduits is arrested once the ring 84 contacts the distal stop 86 at the distal end of the balloon catheter shaft 74. Continued distal movement of the outer catheter 22 and conduits 10 causes the distal portions 28 of the conduits, which are not secured within the outer catheter shaft 22 to bow radially outward to contact or approach the treatment area 4 within inside the vessel wall 5.

In use, the dilatation catheter and delivery device combination is navigated to the intended treatment site 4 through a guide catheter (not shown) and advanced distally to position the deflated balloon 78 within the treatment site 4. It is noted that although the therapeutic substance delivery device 2 and balloon catheter 72 are independently slidable relative to each other, the presence of the distal stop 86 and luer connector fittings at the proximal end of the dilatation catheter prevent the catheter from being withdrawn and separated completely from the outer catheter 22 and array of infusion tubes 10 because the inside diameter of the central lumen of the outer catheter 22 is not large enough to accept the distal stop. As shown in FIG. 10, a balloon 78 is inflated within the treatment area 4 to dilate the stenosis by the same method as any conventional balloon catheter would be used.

After dilatation, the balloon 78 is deflated but the balloon catheter is maintained in position within the treatment area 4 of the vessel 6. The outer catheter and infusion tubes 10 are advanced distally along the catheter shaft 74 and over the deflated balloon 78 until the ring 84 engages the distal stop 86 which arrests distal movement of the distal ends 12 of the conduits 10. Continued distal advancement of the outer catheter 22 and infusion tubes 10 thus causes the distal portions 28 of the infusion tubes to bow radially outward in close proximity to or in contact with the treatment site 4 on the inside vessel wall 5. Once the infusion tubes 10 are expanded radially outward, the therapeutic substance may be perfused from perfusion ports 36 by pressurized delivery through the conduits 10 as described above.

From the foregoing, it will be appreciated that the invention provides a device and method for delivering a therapeutic substance to a treatment site such as the inside surface of a vessel. Localized delivery of one or more therapeutic substances can be achieved simultaneously by an expandable array of conduits that do not require an inflatable member for their expansion to reach the inside surface of a vessel wall. Therefore, the delivery system and method do not risk blocking blood flow through the vessel, enhancing safety and efficacy of the procedure.

It should be understood, however, that the foregoing description of the invention is intended merely to be illustrative thereof and that other modifications, embodiments and equivalents may be apparent to those skilled in the art without departing from its spirit.

Having thus described the invention, what we desire to claim and secure by Letters Patent is:

1. A therapeutic substance delivery device comprising:
    a catheter;
    an elongate shaft having a proximal portion and a distal portion wherein the proximal portion of the shaft passes through the catheter and wherein the shaft defines a lumen; and
    at least one delivery conduit having a lumen in fluid communication with the lumen of the shaft, a proximal portion and a distal portion wherein the proximal portion of the conduit passes through the catheter and the distal portion of the conduit is joined to the distal portion of the shaft and wherein the proximal portion of the conduit is restrained by the catheter to be substantially parallel with the shaft but slidable longitudinally with respect to the shaft whereby when the proximal portion of the conduit is moved relative to the shaft, the distal portion of the conduit buckles and bows in a radially outward direction from the distal portion of the shaft.

2. A therapeutic substance delivery device as defined in claim 1 further comprising a plurality of perfusion ports formed in the distal portion of the conduit.

3. A therapeutic substance delivery device as defined in claim 2 further comprising piercing tubes extending from the perfusion ports.

4. A therapeutic substance delivery device as defined in claim 1 wherein the catheter has a plurality of lumens and the shaft and the conduit reside in independent lumens.

5. A therapeutic substance delivery device as defined in claim 1 further comprising a lock engageable with the shaft to maintain the conduit in a fixed position relative to the shaft.

6. A therapeutic substance delivery device as defined in claim 5 wherein the lock comprises a detachable sleeve engageable around the circumference of the shaft.

7. A therapeutic substance delivery device as defined in claim 5 wherein the lock comprises a sleeve configured to grip the circumference of the shaft.

8. A therapeutic substance delivery device as defined in claim 1 wherein the lumen of the shaft is joined to a manifold in fluid communication with the distal portion of the conduit.

9. A therapeutic substance delivery device as defined in claim 1 wherein the proximal portion of the conduit is joined to a source of a therapeutic substance.

10. A therapeutic substance delivery device as defined in claim 1 further comprising a delivery tube having a proximal end in fluid communication with a source of a therapeutic substance and a distal end in fluid communication with the proximal portion of the conduit.

11. A therapeutic substance delivery device as defined in claim 10 wherein the distal end of the delivery tube is joined and in fluid communication to a manifold which is joined and in fluid communication with the conduit.

12. A therapeutic substance delivery device as defined in claim 1 wherein the conduit assumes a spiral configuration when it is bowed radially outward from the shaft.

13. A therapeutic substance delivery device as defined in claim 1 wherein the conduit contacts tissue to be treated with a therapeutic substance when the conduit is in a bowed configuration and is pressurized to deliver a therapeutic substance.

14. A method of delivering a therapeutic substance to tissue within a patient comprising:
    providing an elongate shaft and at least one delivery conduit having a lumen, a proximal end, a distal end, a proximal portion and a distal portion wherein the distal end is attached to the shaft and at least the proximal portion extends substantially parallel to the shaft and is slidable relative to the shaft, the distal end having at least one perfusion port and a proximal end being in fluid communication with a source of a therapeutic substance;
    inserting the shaft and conduit combination into the patient and navigating the combination through the vessels of the patient so that the distal portion of the conduit is adjacent tissue to be treated;
    moving the conduit and shaft relative to one another such that the conduit bows radially outward from the shaft toward the tissue to be treated;
    pressurizing the therapeutic substance through the lumen of the conduit to eject the substance through the perfusion port, outward to the area of tissue to be treated; and
    rotating the conduit about a longitudinal axis of the shaft while the conduit is in its bowed, radially outward configuration and the therapeutic substance is being, ejected through the perfusion ports.

15. A method of delivering a therapeutic substance to tissue as defined in claim 14 wherein the conduit contacts the tissue to be treated when it is in its bowed radially outward position.

16. A method of delivering a therapeutic substance to tissue as defined in claim 14 wherein the tissue being treated is the inside of a vessel.

17. A therapeutic substance delivery device comprising:
    an elongate shaft having a proximal end and a distal end and having an inflatable member adjacent the distal end thereof;
    a plurality of expandable delivery conduits, each having a proximal end and a distal end, at least portions of which extend substantially parallel with the shaft and are associated with the shaft such that the conduits are expanded by the relative movement of the shaft and the conduits and the inflatable member is expanded by pressurized fluid; and
    a ring slidably mounted on the elongate shaft and joined to the distat end of each conduit.

18. A therapeutic substance delivery device as defined in claim 17 further comprising a stop at the distal end of the elongate shaft distal to the inflatable member against which the ring abuts to terminate slidable movement of the ring and conduits relative to the shaft whereby a distal sliding force placed on the conduits in a distal direction, after the ring abuts the stop, causes the conduit to bow radially outward from the shaft.

19. A therapeutic substance delivery device as defined in claim 18 wherein the conduit assumes a spiral contour while in its bowed configuration.

20. A method of dilating a vessel and delivering a therapeutic substance to the vessel comprising:

provi​ding a balloon dilatation catheter having a shaft with proximal and distal ends and a stop at the distal end and at least one conduit having proximal and distal ends and a lumen extending therethrough with a plurality of perfusion ports adjacent its distal end;

a ring slidable about the shaft and joined to the distal end of the conduit;

inserting the catheter and conduit into a patient and navigating it to a treatment site within a vessel;

inflating the balloon of the balloon catheter at the treatment site to dilate the vessel while the ring and conduit are proximal to the balloon;

deflating the balloon and advancing the ring and conduit distally over the catheter shaft so that the ring is distal to the balloon and the perfusion ports of the conduit are located at the treatment site;

applying a force on the conduit in a distal direction so that the ring abuts the stop at the distal end of the catheter causing the conduit to bow radially outward toward the vessel wall;

delivering a therapeutic substance through the lumen of the conduit such that it perfuses through the perfusion ports to the area of the treatment site.

21. A method of dilating a vessel and delivering a therapeutic substance as defined in claim 20 wherein the conduit assumes a spiral configuration while in its bowed, radially outward configuration.

22. A method of dilating a vessel and delivering a therapeutic substance to a vessel as defined in claim 20 further comprising rotating the delivery conduit while in its bowed, radially outward configuration and a therapeutic substance is delivered through a perfusion port.

23. A dilatation and therapeutic substance delivery device comprising:

a balloon catheter having a shaft with a proximal end and a distal end and a balloon mounted adjacent the distal end; and at least one delivery conduit having a proximal end and a distal end, a proximal portion and a distal portion, wherein the conduit extends substantially parallel to the catheter shaft and at least the proximal portion of the conduit being slidable relative to the catheter shaft and the distal end of the conduit being fixedly attached to the catheter shaft proximal to the balloon.

24. A dilatation and therapeutic substance delivery device as defined in claim 23 further comprising an outer catheter shaft through which is received the balloon catheter shaft and the delivery conduit.

25. A dilatation and therapeutic substance delivery device as defined in claim 24 wherein the conduit is fixed relative to the outer catheter and the dilatation catheter is slidable relative to the outer catheter.

26. A dilatation and therapeutic substance delivery device as defined in claim 24 wherein both the conduit and the dilatation catheter are slidable relative to the outer catheter.

27. A dilatation and therapeutic substance delivery device as defined in claim 24 wherein the outer catheter has a plurality of lumens through which the balloon catheter and conduit extend.

28. A dilatation and therapeutic substance delivery device as defined in claim 24 further comprising a lock circumferentially mountable around the shaft of the balloon catheter and engageable with the shaft to prevent relative movement between the balloon catheter shaft and the conduit.

29. A method of dilating a treatment site within a vessel and delivering a therapeutic substance to the treatment site comprising:

providing a balloon dilatation catheter having a shaft with proximal and distal ends and a balloon mounted adjacent the distal end and at least one delivery conduit having proximal and distal ends and proximal and distal portions with a plurality of perfusion ports along the distal portion and the proximal end being in fluid communication with a source of a therapeutic substance, the distal end of the conduit is joined to the shaft of the balloon catheter such that relative movement of the conduit and balloon catheter shaft causes at least the distal portion of the conduit to bow radially outward from the catheter shaft;

inserting the balloon catheter and delivery conduit into a patient and then navigating it so that the balloon is adjacent the treatment site;

inflating the dilatation balloon to dilate the vessel;

deflating the balloon after the vessel is dilated and advancing the balloon catheter and conduit distally so that the distal portion of the conduit and perfusion ports are adjacent the treatment site;

advancing the conduit distally relative to the balloon catheter to cause the distal portion of the conduit to bow radially outward toward the treatment site;

delivering a therapeutic substance through the conduit so that it perfuses through the perfusion ports.

30. A method of dilating a vessel and delivering a therapeutic substance to a treatment site within a vessel as defined in claim 29 further comprising:

engaging a lock on the catheter shaft to maintain the conduit in its bowed, radially outward configuration.

31. A method of dilating a treatment site within a vessel and delivering a therapeutic substance to the delivery site as defined in claim 29 wherein a lock is placed about the catheter shaft adjacent the proximal end to restrain the conduit and catheter shaft from relative movement.

32. A method of dilating a vessel at a treatment site and delivering a therapeutic substance to the delivery site as defined in claim 29 wherein the conduit assumes a spiral configuration when placed in its bowed, radially outward configuration.

33. A method of dilating a vessel at a treatment site and delivering a therapeutic substance to the treatment site as defined in claim 29 further comprising: rotating the conduit and balloon catheter shaft about the axis of the catheter shaft while the conduit is in its bowed, radially outward configuration and is delivering a therapeutic substance through the perfusion ports.

* * * * *